United States Patent
Li et al.

(10) Patent No.: US 7,661,326 B2
(45) Date of Patent: Feb. 16, 2010

(54) APPARATUS FOR ASPIRATING AND DISPENSING LIQUIDS IN AN AUTOMATED ANALYZER

(75) Inventors: William W. Li, Miami, FL (US);
William J. Casey, Boca Raton, FL (US);
Craig R. Veiner, Miami, FL (US);
Carlos R. Gonzalez, Pinecrest, FL (US);
Jose M. Cano, Miami, FL (US);
Roberto Del Valle, Coral Gables, FL (US);
Santiago Galvez, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 450 days.

(21) Appl. No.: 11/553,107

(22) Filed: Oct. 26, 2006

(65) Prior Publication Data

US 2008/0098828 A1 May 1, 2008

(51) Int. Cl.
*G01N 1/00* (2006.01)
(52) U.S. Cl. .................................... 73/863.73
(58) Field of Classification Search ........................ None
See application file for complete search history.

(56) References Cited

U.S. PATENT DOCUMENTS

| 4,896,546 | A | | 1/1990 | Cabrera et al. |
| 5,158,751 | A | * | 10/1992 | del Valle et al. ............. 422/103 |
| 5,460,055 | A | | 10/1995 | Parker |
| 5,691,486 | A | * | 11/1997 | Behringer et al. ......... 73/863.73 |
| 6,322,752 | B1 | | 11/2001 | Siddiqui et al. |
| 2003/0152493 | A1 | * | 8/2003 | Lefebvre .................... 422/100 |
| 2006/0213257 | A1 | * | 9/2006 | Togashi et al. ............. 73/61.55 |
| 2006/0216208 | A1 | | 9/2006 | Li et al. |

* cited by examiner

*Primary Examiner*—Robert R Raevis
(74) *Attorney, Agent, or Firm*—Warren W. Kurz; Mitchell E. Alter (57) ABSTRACT

Apparatus for aspirating and dispensing liquid samples in an analytical instrument, e.g., a hematology instrument, includes a liquid-sampling valve that, while operating to segment and position for dispensing one or more precise volumes of a liquid sample that has been aspirated into the valve by a pump, simultaneously enables the apparatus to be operated in an aspirate/dispense (suck-and-spit) mode in which a liquid sample can be selectively driven through the valve in opposite directions by a pump, e.g., a syringe pump.

6 Claims, 8 Drawing Sheets

FIG. 3D

APPARATUS FOR ASPIRATING AND DISPENSING LIQUIDS IN AN AUTOMATED ANALYZER

BACKGROUND OF THE INVENTION

1. Field of the Invention

The present invention relates to improvements in apparatus for aspirating liquids, e.g., whole blood, from a sample container and for dispensing precise volumes of the aspirated liquid to multiple reaction chambers and/or baths for subsequent mixing in order to prepare the aspirated liquid for analysis or further processing, as appropriate. The invention is particularly useful in the fields of hematology, flow cytometry and blood chemistry in which it is often necessary to dispense, with high precision, relatively tiny volumes (e.g., 1-30 microliters) of whole blood and/or a prepared blood sample.

2. The Prior Art

In conducting tests on samples of biological liquids, such as blood, urine and other body liquids, it is common to provide the sample to an automated analyzer in a sealed test tube or vial. Upon receiving the test tube, the analyzer automatically transports it to an aspiration station where the sharpened tip of an aspiration probe pierces the seal (typically a rubber stopper) and enters the sample volume. After aspirating a portion of the sample from its container, relatively tiny aliquots of the sample, each having a volume of between, say, 1 and 30 microliters, are subsequently dispensed to different reaction chambers and/or baths within the analyzer for processing and/or analysis. While some quantitative analyses, e.g., red and white blood cell counts, require extreme precision in the accuracy of the sample volume dispensed, other, more qualitative, analyses do not require such precision in the dispensing volume.

In general, the liquid aspirating and dispensing apparatus of automated blood analyzers is one of two types: (i) those that aspirate a blood sample into a blood sampling valve or "BSV" that serves to segment the aspirated liquid into multiple precise aliquots for subsequent dispensing, and (ii) those that use a precision syringe pump connected to the aspiration probe to both suction out a portion of the sample from its container, and then expel or dispense multiple metered volumes of the aspirated sample though the same aspiration probe to a reaction chamber or bath. The latter type of aspirating/dispensing apparatus is often referred to as a "suck and spit" apparatus, for obvious reasons.

In many of the automated hematology instruments manufactured by Beckman Coulter, Inc. (e.g. the Models MAXM™ and LH750™ blood analyzers), multiple BSVs are used to segment precise volumes of an aspirated blood sample for analysis. A typical BSV used in these instruments takes the form of a multi-element shear valve assembly, comprising two or more confronting planar pads or plates that are selectively movable relative to each other to define two different configurations; viz., (a) a "loading" configuration in which an aspirated blood sample can be transmitted entirely through the internal and external passageways of the valve assembly, and (b) a "segmenting/dispensing" configuration in which precise volumes of sample passing through certain passageways of the valve assembly (referred to as the "aliquoting chambers") are segmented or isolated from the rest of the blood sample filling the valve assembly, and positioned to be chased or expelled from the valve by another liquid, such as a diluent or reagent that is used in the sample preparation process. Often, one of the pads has a bore hole passing through it that defines a relatively small aliquoting chamber; alternatively, a planar surface of one of the valve pads is provided with a surface groove that precisely defines, together with a confronting planar surface of an adjacent pad, a desired volume of sample liquid to be dispensed. It is also common that a BSV is provided with one or more external loops of tubing that selectively communicate with internal passages of the BSV, the internal volume of these loops define additional, relatively large, aliquoting chambers that become filled with blood when the valve is in its loading configuration. Various types of BSVs of the type described have been devised, and many have been disclosed in the patent literature; see, e.g., the disclosures of the commonly assigned U.S. Pat. Nos. 4,896,546; 5,158,751; and 5,460,055.

In terms of the preciseness of the sample volumes dispensed, BSVs are the "gold standard." It is a relatively simple matter to size the aliquoting chambers in such devices to achieve a precise volume. But, since BSVs comprise an assembly of precision parts that are both difficult to manufacture and to assemble in a manner such that the valve operates as intended and without leakage, BSVs add considerable cost to a liquid dispensing system. Further, due to the physical size of conventional BSVs and their related hardware, these devices are commonly located some distance from the sample-aspiration probe of the analyzer, and an appropriate length of tubing is used to connect the probe with each sampling valve. Thus, it will be appreciated that a relatively sizable volume of sample (e.g., about 250-300 microliters) must be aspirated from the sample container in order to fill a series of BSVs and their interconnecting tubing. Typically, out of the aspirated sample volume, no more than about 30% is ever used for the analysis, with the remainder being eventually flushed to waste. In addition to being located at a considerable distance from the aspiration probe, BSVs are often located at a considerable distance from the reaction chambers and baths that make use of the segmented samples they provide; thus, in addition to requiring a relatively large sample, conventional BSVs require a large volume of a non-reactive diluent or other fluid used to chase the segmented sample volumes through tubing connecting the BSVs and the reaction chambers and baths.

Because of their requirement of relatively large sample volumes, hematology instruments that incorporate BSVs of the above type sometime include an auxiliary aspiration probe that is directly coupled to a BSV without any intervening (sample-consuming) tubing. This auxiliary aspiration probe is non-movable within the instrument, and it is usually located outside the instrument housing so that an open container of sample can be manually presented to the probe for aspiration. Thus, upon manually moving a sample container so that the tip of the auxiliary probe is immersed in the sample, the latter is aspirated directly into the BSV from the probe with little waste of the sample. While this auxiliary probe and BSV assembly can be used to aspirate and precisely segment very small volumes of sample, as may be obtained from infants and newborns, its requirement of a manual presentation of the sample dramatically reduces the throughput of the instrument. Further, the need to present a sample for aspiration in a non-sealed container increases the potential of operator exposure to infectious diseases.

As regards the above-mentioned syringe pump (suck-and-spit) approach to aspirating and dispensing liquid, this approach is clearly less costly and is less complicated than the BSV approach. Further, it is advantageous from the standpoint that it less wasteful of the sample to be analyzed. The syringe pump approach relies on the precision movement of a plunger or diaphragm in a fluid path. As the plunger or diaphragm moves in a pulling (sucking) direction, a negative pressure is produced in the probe, causing the sample to be drawn into the probe and its associated tubing through the probe tip. As the plunger or diaphragm moves in the pushing (spitting) direction, a positive pressure is generated that will dispense (or spit) a portion of the just-aspirated sample through the probe tip. Obviously, the accuracy of this approach to aspirating and dispensing a sample depends on the accuracy of moving the plunger or diaphragm in opposite directions. While stepper-motor controlled syringe pumps are known that can satisfy the volume accuracy requirements of some of the sample-preparation processes to be performed, the task of accurately dispensing samples of ten microliters or less can be problematic, especially when the volume to be dispensed approximates the residual volume in the probe after dispensing. Thus, while the syringe pump approach afford several advantages over the BSV approach, the volume accuracy of each aliquot dispensed is difficult to repeatedly control.

In the commonly assigned U.S. Pat. No. 6,322,752 to I. T. Siddiqui, a "hybrid" apparatus is disclosed for aspirating and dispensing blood samples and the like. In one embodiment, a shear valve assembly (i.e., a BSV) is connected directly to an aspiration probe and is movable therewith. The probe is movable within the instrument in at least two perpendicular planes, one to enable it to move into and out of a sample container to access the liquid therein, and one to enable the probe to move relative to various reaction chambers and baths where it is to dispense precise volumes of the aspirated liquid. In a loading configuration, the shear valve enables the aspirated sample to be drawn through the probe, then through an aliquoting chamber in one of the shearing pads of the assembly, and finally through tubing on the upstream side of the valve assembly to a blood detector located between an aspirating pump and the shear valve. Upon sensing that the leading edge of the aspirated volume has reached a point upstream of the shear valve, the latter is operated in its "segmenting/dispensing" configuration in which it serves to (a) isolate that portion of the aspirate liquid within its aliquoting chamber and (b) trap aspirated liquid within the interior volume of the aspirating probe; in this manner, the assembly provides two precise aliquots of liquid for dispensing. Upon operating the shear valve in its segmenting/dispensing configuration, the trapped aliquots of liquid can be chased from the aliquoting chambers within the shear valve and probe interior by connecting them to different sources of positive pressure (e.g., diluent pumps). At the same time, all of the non-used blood that has been aspirated from the sample container and used to fill the shear valve and the lines upstream thereof is flushed to waste.

While the hybrid apparatus described in the above patent is capable of dispensing highly precise volumes of sample for analysis, this apparatus may be considered disadvantageous in that it can only dispense a relatively small overall volume of blood sample, i.e., that contained in the probe and in the aliquoting chamber of the shear valve. Further, it is wasteful of a considerable amount of sample on the upstream side of the shear valve. Still further, once the shear valve has operated to segment the different aliquots of sample, the aspiration probe can do no more than dispense the volume of sample liquid trapped in the shear valve and in the probe interior; it cannot be used simultaneously to achieve other objectives in the instrument.

SUMMARY OF THE INVENTION

In view of the foregoing discussion, an object of this invention is to provide an improved hybrid apparatus for aspirating and dispensing a biological liquid that affords the accuracy of the above-noted BSV apparatus, and the low volume feature of the syringe pump (suck-and-spit) apparatus.

Another object of this invention is to provide an apparatus for aspirating, segmenting and dispensing a liquid sample that can make use of virtually all of a sample liquid aspirated from a sample container and thereby reduce the unused volume that is characteristic of the prior art apparatus.

Still another object of this invention is to provide an improved fluid-sampling valve that enables a liquid aspirating and dispensing apparatus to operate simultaneously in a "suck-and-spit" mode while precise volumes of liquid are dispensed from aliquoting chambers within the fluid-sampling valve.

According to a first aspect of the invention, a new and improved liquid-sampling valve is provided for use in a method and apparatus for aspirating a liquid (e.g., whole blood) from a container and for dispensing a plurality of precise aliquots of such liquid to different chambers, e.g., for preparation for analysis. In contrast with known and existing BSV-type valves, the liquid-sampling valve of the invention is structured to enable an aspiration probe (to which the valve is operably connected) to be used in an aspirating-and-dispensing (i.e., suck-and-spit) mode while the valve simultaneously operates to store and position for dispensing one or more precise aliquots of a liquid that has been previously aspirated into the valve through the aspiration probe. Preferably, the new liquid-sampling valve comprises a multi-element shear valve assembly that defines one or more aliquoting chambers in which precise volumes of a liquid sample can be temporarily stored. Upon aspirating a liquid sample into the aliquoting chamber(s) of the liquid-sampling valve and operating the valve in a manner acting to segment and position the fluid aliquot(s) for subsequent dispensing, the valve continues to enable additional liquid sample to be selectively aspirated or dispensed through the valve and its associated aspiration probe, under the force provided by a pump located upstream of the valve, preferably by the same pump used to initially aspirate the biological liquid into the aliquoting chamber(s) of the valve.

According to a second aspect of the invention, new and improved apparatus is provided aspirating and dispensing a liquid sample in an automated analytical instrument. Such apparatus comprises (a) an aspiration probe adapted to enter a sample container to aspirate a liquid sample (e.g., a blood sample) within such container, (b) a transport system for selectively advancing the aspiration probe in mutually perpendicular planes so that the probe can aspirate (or dispense) liquid from (or to) different containers spaced apart, (c) a liquid-sampling valve operatively connected to the aspiration probe, such liquid-sampling valve defining at least one aliquoting chamber for temporarily storing a precise volume of liquid sample to be dispensed, and (d) a pump operatively connected to the liquid-sampling valve and selectively operable to either (i) draw a liquid sample through the aspiration probe and through the liquid-sampling valve to fill the aliquoting chamber, or (ii) to dispense aspirated liquid sample through the aspiration probe. The liquid-sampling valve is designed to be selectively operable in either (i) an aspiration mode in which a liquid sample aspirated by the aspiration probe under the influence of the pump will pass through the liquid-sampling valve while simultaneously filling or "loading" the aliquoting chamber(s) thereof, or (ii) a segment/dispense mode in which liquid within the aliquoting chamber(s) is positioned to be dispensed from the shear valve by an external force, while liquid can be either aspirated or dispensed through the aspiration probe and through the liquid-sampling valve by the pump.

The invention and its advantages will be better understood from the ensuing detailed description of preferred embodiments, reference being made to the accompanying drawings wherein like reference characters denote like parts.

DETAILED DESCRIPTION OF PREFERRED EMBODIMENTS

Figure 1A:
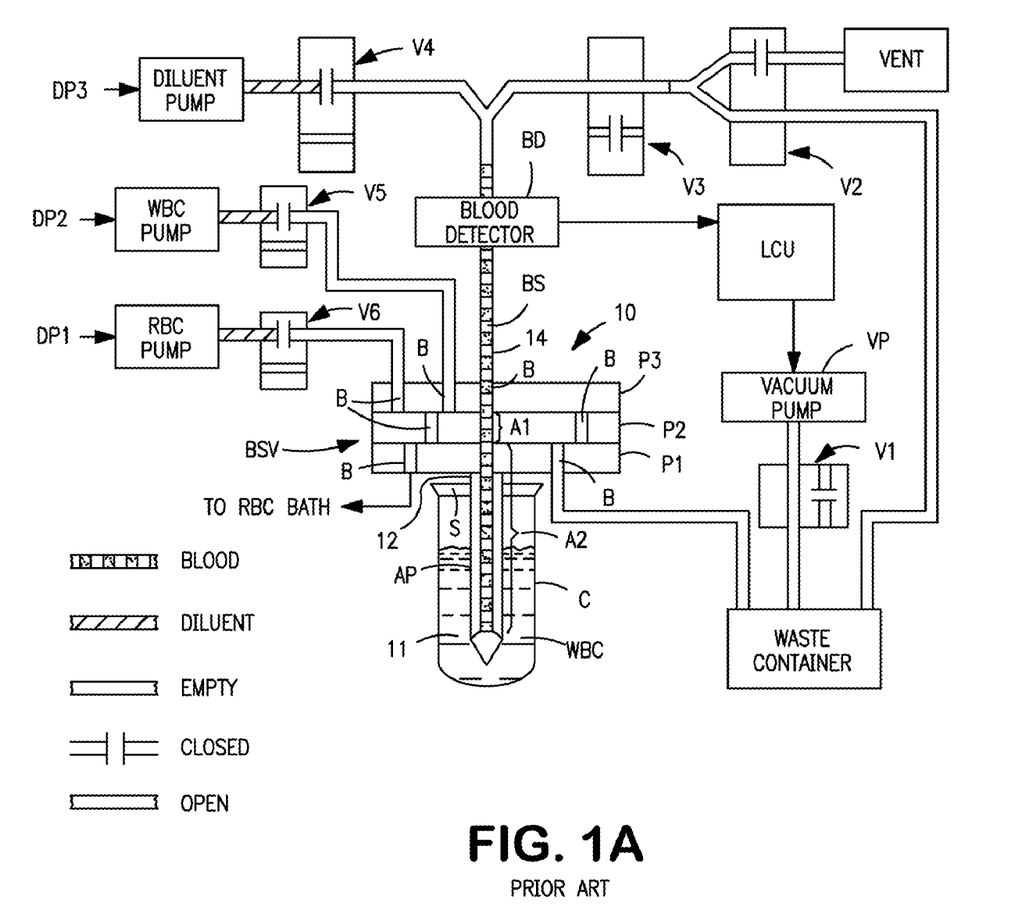
FIGS. 1A-1C are schematic illustrations showing the operation of a hybrid prior art apparatus for aspirating and dispensing a liquid.
Figure 1B:
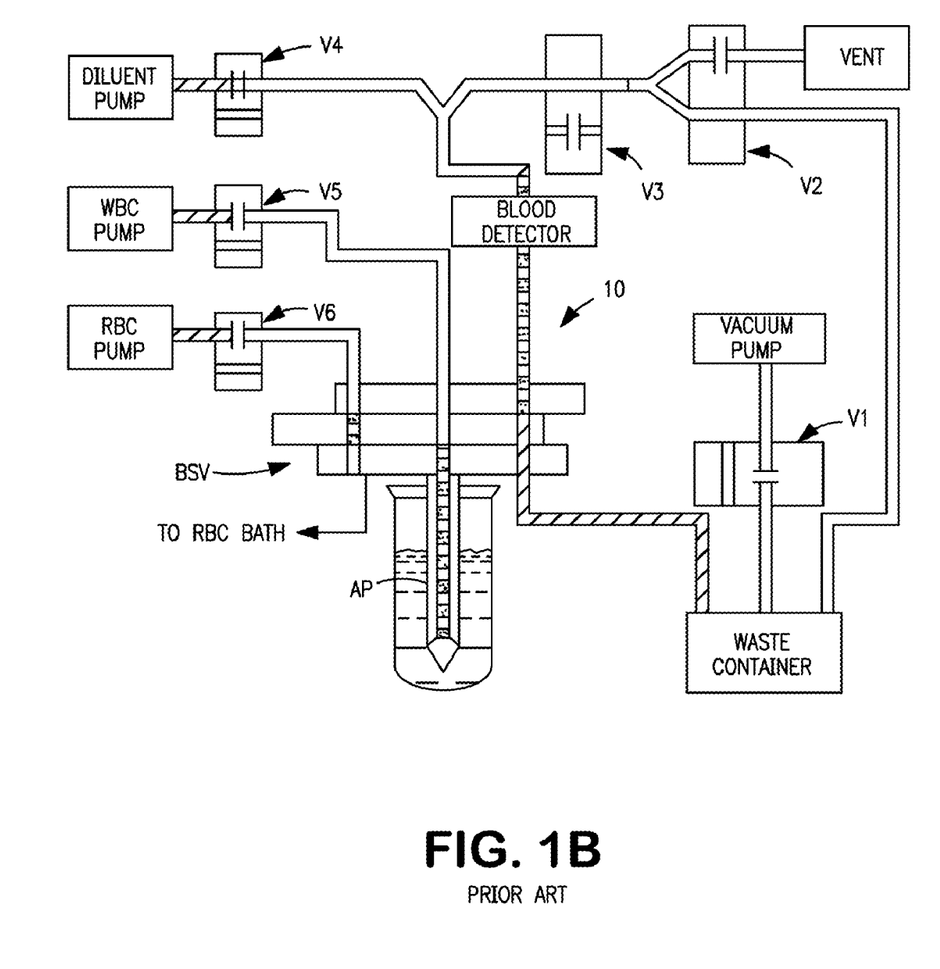
Figure 1C:
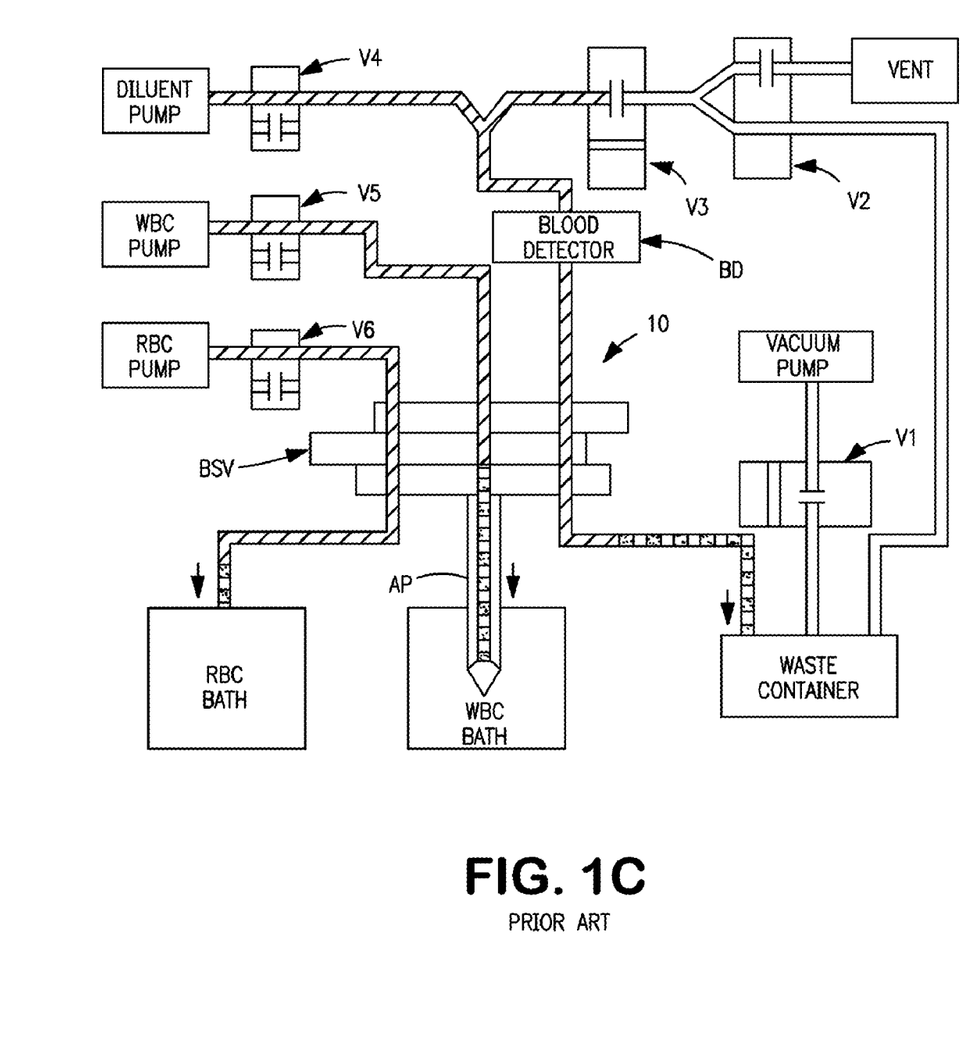

Referring now to the drawings, FIGS. 1A-1C schematically illustrate a prior art apparatus 10 for aspirating and dispensing a whole blood sample WBS disposed in a container C having a rubber seal S. Such apparatus is part of a conventional automated instrument system that is designed to count, differentiate and otherwise analyze different types of red and white blood cells comprising the whole blood sample. The blood aspirating and dispensing apparatus, which is more thoroughly described in the above-noted U.S. Pat. No. 6,322,752, comprises a hollow aspiration probe AB having a sharpened distal end 11 that serves to penetrate the seal S on the sample container to access the liquid sample therein. The aspiration probe has a proximal end 12 that is rigidly connected to a blood-sampling valve BSV. In this apparatus, the aspiration probe and its rigidly connected BSV are mounted for lateral movement, i.e., movement perpendicular to the vertical direction in which they move to access sample in a container, whereby the aspirating probe can dispense its sample aliquots into chambers laterally spaced from the sample container. As illustrated, the BSV is essentially a shear valve assembly comprising three confronting pads P1, P2 and P3, each having a plurality of bore holes B, strategically located therein. The shear pads are movable with respect to each other to selectively cause their respective bore holes to become either aligned, whereby liquid can flow between adjacent pads, or misaligned, whereby such flow of liquid is prevented. In FIG. 1A, the shear valve is shown in a sample-loading configuration in which the blood sample can be drawn or aspirated, under the negative pressure of a vacuum pump VP, into and through three aligned bore holes in the three shear pads, and then into to a conduit 14 connected to the aligned bore hole in the top pad P3. When the aspirated blood in conduit 14 reaches a blood detector BD a signal is transmitted to a programmable logic and control unit (LCU) that controls the operation of all system components, including the BSV, the vacuum pump VP, open/close valves V1-V6, and diluent pumps DP1-DP3. The LCU then operates to deactivate the vacuum pump and to adjust the relative positions of shear pads P1-P3 to the positions shown in FIG. 1B, whereby two precise aliquots (A1 and A2) of whole blood are segmented or isolated from the aspirated volume of blood for analysis. At the same time, different bore holes in the shear valve pads become aligned, whereby the precise aliquots A1 and A2 of whole blood can be dispensed for analysis. The smaller aliquot A1, defined by the internal volume of a bore hole formed in the intermediate pad P2, is used for determining red blood cell (RBC) count, and the larger aliquot A2, defined by the internal volume of the aspiration probe downstream of the intermediate pad P2, is used for white blood cell (WBC) count and analysis. As will be appreciated, the volume of aliquot A1 is defined by the thickness of pad P2 and the diameter of the bore hole therein. Typically, the volume of aliquot A1 for RBC analysis is selected to be between 1 and 10 microliters. The relatively large volume of aliquot A2 is defined by the internal volume of the aspiration probe AP, plus the volume of the bore hole in shear pad P1 through which the aspirated sample is aspirated. Typically, this volume of aliquot is between 200 and 300 microliters. After a suitable delay, the LCU operates apparatus 10 in a dispensing mode (shown in FIG. 1C) in which valves V4-V6 are opened, and the diluent pumps DP1-DP3 are activated to chase the aliquots of sample to different baths for sample preparation, and to flush the non-used blood sample to a waste container. More specifically, the RBC pump DP1 operates to dispense a predetermined volume of diluent through aliquot A1 to RBC bath from which a diluted and mixed RBC sample is extracted and analyzed. The WBC pump DP2 operates to dispense a predetermined volume of diluent through aliquot A2 to a WBC bath in which different reagents (e.g. lyse, stain, etc.) are added to provide a suitable sample for WBC analysis. And the diluent pump P3 operates to flush conduit 26 of the blood sample therein.

From the foregoing description, it may be appreciated that the apparatus schematically illustrated in FIGS. 1A-1C is disadvantageous from the standpoint that it wastes a considerable volume of the aspirated blood sample, viz., all of the blood sample positioned upstream of the BSV. As shown in FIG. 3C, all of such blood is eventually flushed to waste by the diluent pump DP3. Further, it will be noted that, until the shear valve and aspiration probe are emptied of their respective contents, the apparatus cannot be used for other purposes, e.g., the aspirating probe cannot be used in a suck-and-spit mode to further process the sample.

Figure 2:
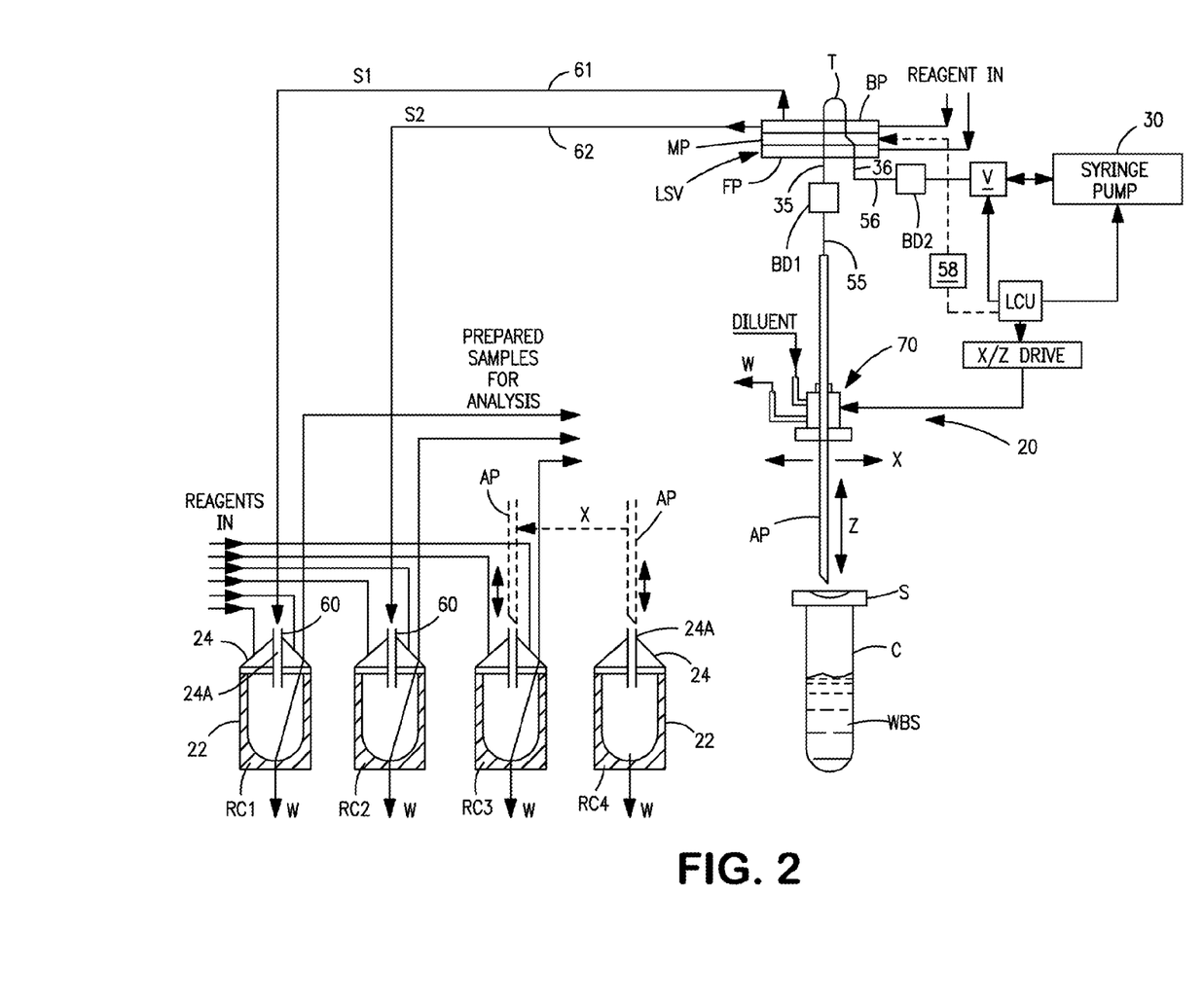
FIG. 2 is a schematic illustration of a portion of a blood analyzing instrument embodying the present invention.

Now, in accordance with the present invention, there is provided a liquid-aspirating and dispensing apparatus 20 that overcomes the above-noted shortfalls of the liquid aspirating and dispensing apparatus shown in FIGS. 1A-1C. Referring to FIG. 2, the apparatus 20 of the invention is depicted as being embodied in a portion of a blood-analyzing system that includes a plurality of reaction chambers, RC1-RC4, in which predetermined volumes of a whole blood sample are to be mixed with various reagents to condition the samples for a particular type of analysis. For example, in reaction chamber RC1, a relatively minute and precise volume (e.g., about 15 microliters) of whole blood may be mixed with a predetermined volume of a suitable diluent to provide a precisely diluted sample that is useful in determining the red blood cell count of the sample. In reaction chamber RC2, a larger, yet precise, volume of whole blood may be mixed with a suitable lytic reagent, a stabilizer and a diluent to provide a white cell sample adapted for a differential analysis of the various types and concentrations of white cells in the sample. In reaction chamber RC3, a volume of blood sample may be mixed with a fluorescent dye adapted to differentially stain or otherwise tag a certain type of cell, e.g. reticulocytes. Upon tagging the such cells in chamber RC3, a predetermined volume is to be transferred to reaction chamber RC4 where the tagged cell sample is further prepared (e.g., diluted) for analysis. As shown, each reaction chamber comprises a cup portion 22 that is sealed by a lid portion 24 having a central opening 24A adapted to receive a predetermined volume of blood sample. Additionally, the lid portions of the reaction chambers are provided with a plurality of ports through which various reagents may be introduced for reaction with the sample, and through which the prepared samples may be extracted from the chambers for analysis. Each reaction chamber has a port at its base through which the residual contents (after removing a portion for analysis) can be flushed to waste W.

Still referring to FIG. 2, the liquid aspirating and dispensing apparatus 20 of the invention comprises an aspirating probe AP, a new and improved liquid-sampling valve LSV, and a bi-directional pump 30. The aspirating probe has a sharpened distal end adapted to puncture a seal S atop the sample container C. The aspiration probe is mounted, in a conventional manner, for movement in vertical and lateral directions, Z and X, respectively, so as to enable the probe tip to enter either the sample container C or any one of the reaction chambers RC1-RC4. Suitable apparatus, i.e., an X/Z drive mechanism, for movably-mounting the aspiration probe for such movement is disclosed, for example, in the commonly assigned U.S. Patent Application Publication No. US-2006-0216208 filed Mar. 23, 2005, the subject matter of which is incorporated herein by reference. Pump 30 is preferably a conventional syringe having a movable actuator that, in moving in a first direction aspiratees liquid through the aspiration probe, and in moving in a first direction aspirates liquid through the aspiration probe, and in moving in an oppsoite direction, dispenses liquid from the probe tip. Thus, the aspiration probe of apparatus 20 is used to both aspirate and dispense sample material.

A key element of apparatus 20 is the liquid-sampling valve LSV which is rigidly mounted at a suitable location within the instrument frame. Unlike the BSV's of the prior art, the liquid-sampling valve of the invention enables the aspiration probe to continue operating in an aspirating/dispensing mode, in which liquid can pass in either direction through the valve, after the valve has operated to position its aliquoting chambers so as to be emptied by a reagent or diluent that is caused to pass through such chambers and thereby chase the stored liquid to a reaction chamber or the like. The various components of liquid-sampling valve and its operation will be best understood with reference to the exploded perspective views of FIGS. 3A-3D.

Figure 3A:
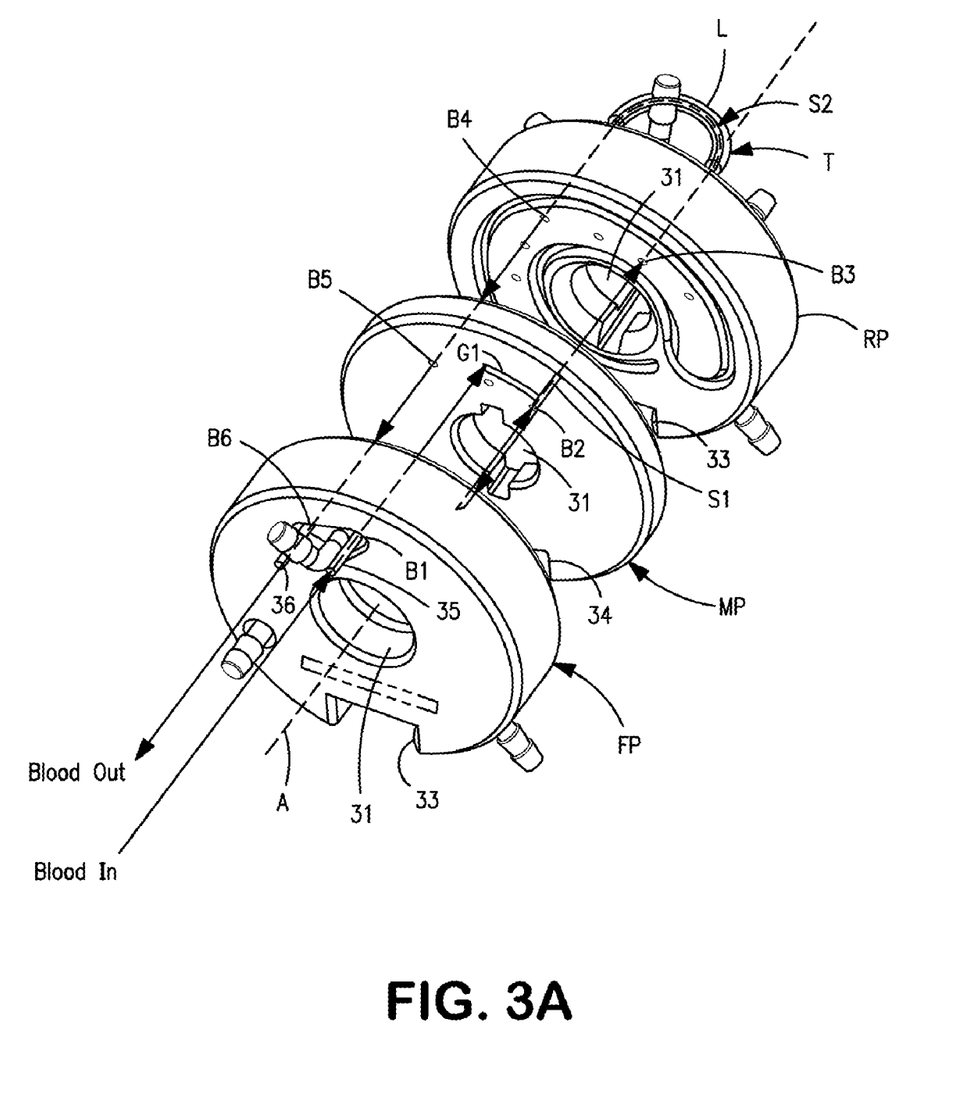
FIGS. 3A-3D are exploded perspective illustrations of a preferred liquid-sampling valve used in the FIG. 2 apparatus.
Figure 3B:
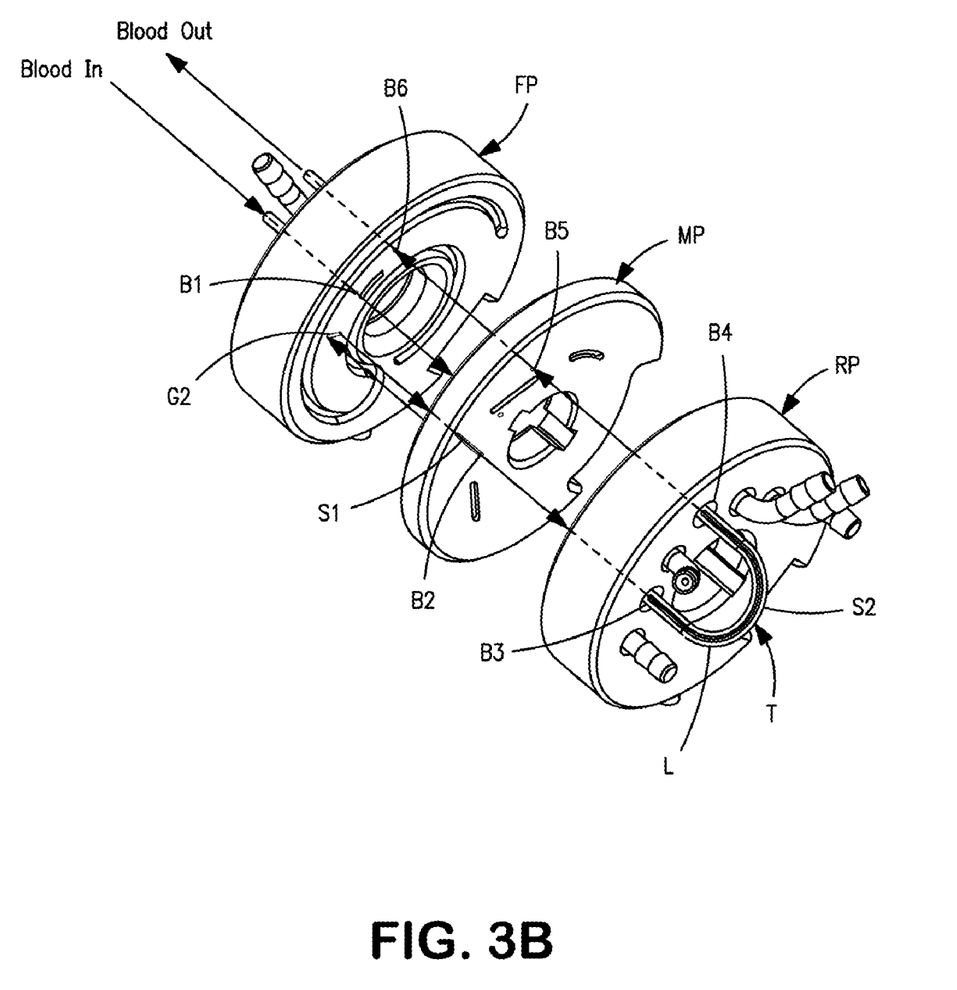
Figure 3C:
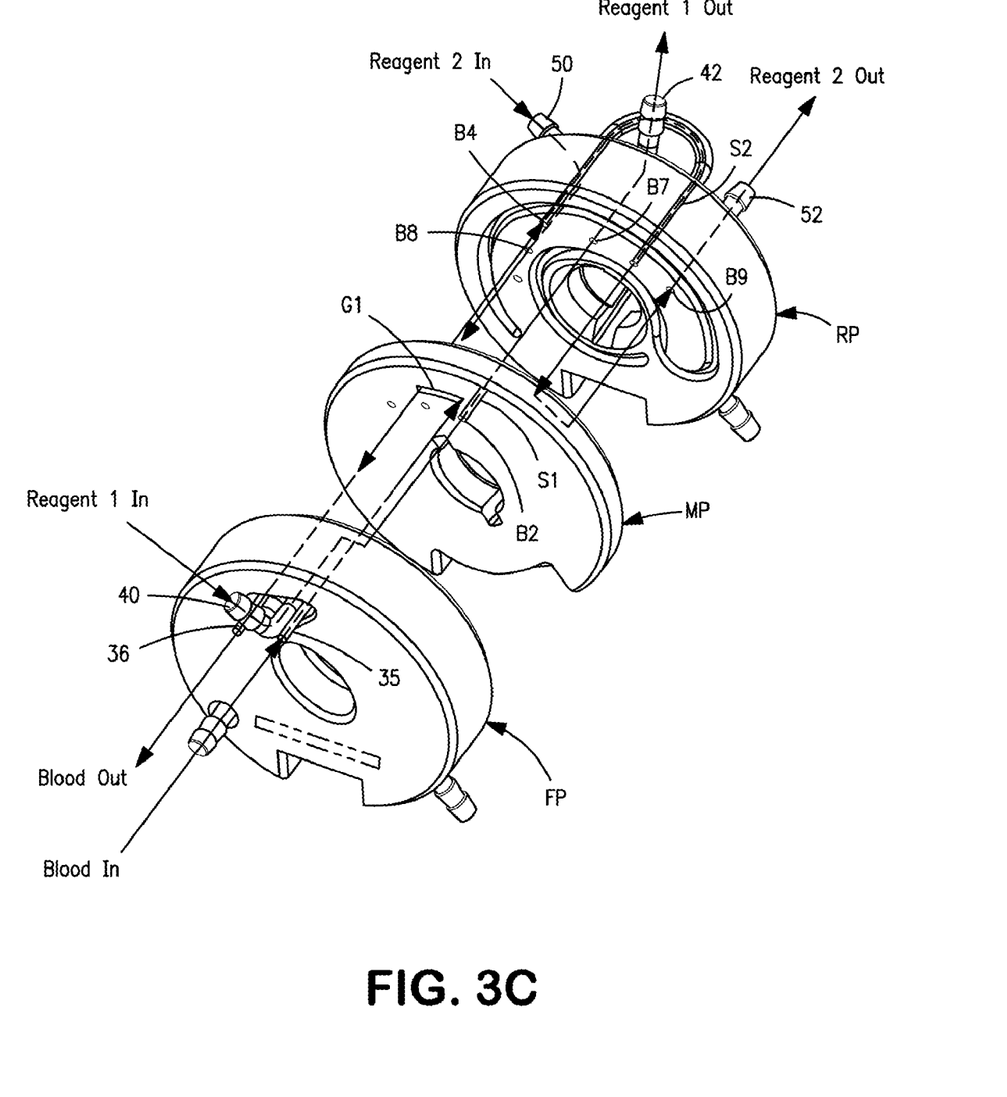
Figure 3D:
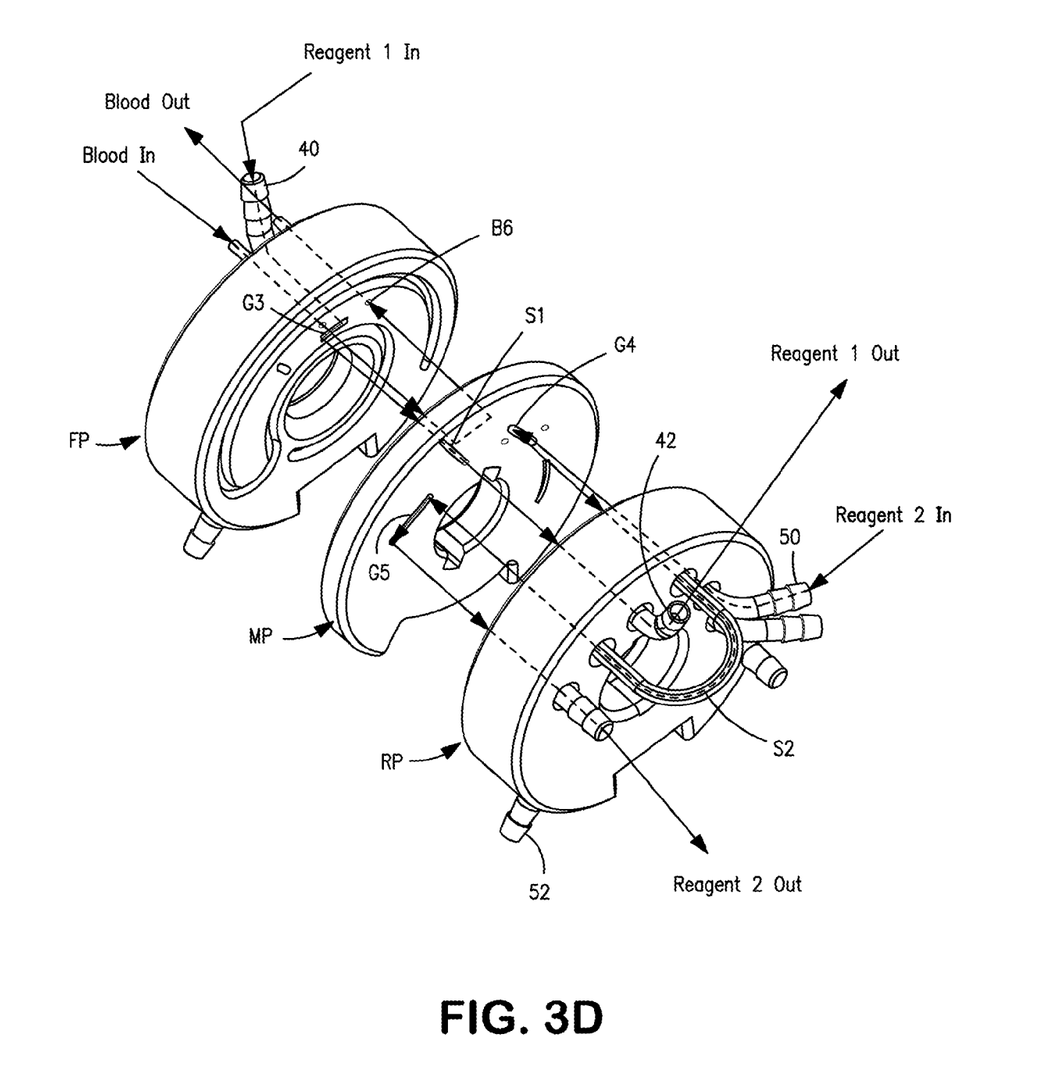

FIGS. 3A and 3B are front and rear views, respectively, illustrating the relative positions of the valve components while the aliquoting chambers of the valve are being filled or "loaded" with sample liquid. FIGS. 3C and 3D are front and rear views, respectively, illustrating the same valve components while sample aliquots are being dispensed from the valve. As is apparent from the drawings, the liquid-sampling valve is a shear valve assembly comprising three confronting, disk-shaped, valve pads, i.e., a front pad FP, a middle pad MP and a rear pad RP. In use, the three pads are contiguously arranged on a shaft (not shown) that passes through a central opening 31 in each pad. An elongated key member, not shown, engages identical slots 33 in the periphery of the front and rear pads and acts to prevent these pads from rotating on their supporting shaft. The same key member engages a larger slot 34, best shown in FIGS. 3B-3C, formed in the periphery of the middle pad; because the key is narrower than slot 34, the middle pad is enabled to rotate through an angle of about 15 or 20 degrees, the extend of such movement being determined by the width of slot 34. Preferably, each of the pads is made of a non-reactive ceramic material, and the planar, confronting surfaces of the pads are polished to prevent leakage of liquid from ports and passageways within the valve assembly when the pads are contiguously arranged.

The sampling valve illustrated in the drawings is designed to provide two precise aliquots, S1 and S2, of a blood sample (or other liquid) for analysis or processing. Aliquod S1 is significantly smaller than S2 and its volume is defined by the volume of a bore hole B2 formed directly through the middle pad MP; thus, bore hole B2 is the aliquoting chamber for S1, and its volume is determined, of course, by the pad thickness and the bore hole diameter. Aliquot S2 is defined, in part, by the internal volume of an arcuate external tube T which is in the form of a loop L extending from and returning to two spaced bore holes B3 and B4 formed in the rear pad RP. Thus, the total volume of aliquot S2 is the sum of the internal volume of external tube T and the respective volumes of bore hole B2 and B3. Note, in FIG. 3B, bore holes B3 and B4 appear relatively large in diameter owing to a counter-sunk region surrounding each hole to facilitate the mounting of the looping tube on the rear pad.

Still referring to FIGS. 3A and 3B, a port 35 extending forwardly of the exterior surface of front pad FP is connected to the aspiration probe AP by a flexible conduit, not shown. Port 35 is aligned with a bore hole B1 formed in the front pad. Thus, in its sample-loading mode, an aspirated liquid sample will pass through bore hole B1 and enters a surface groove G1 formed in the forward-facing surface of the middle pad MP. Groove G1 is arcuate in shape and its center of curvature coincides with the central axis A of the support shaft. Groove G1 faces a planar surface on the rear side of the front pad FP and thereby defines an arcuate passageway through which the sample passes. Confronting groove G1 is a radially-extending groove G2 in the rearward-facing surface of the front pad FP. And confronting a portion of the groove G2 is the bore hole B2 defining sample aliquot S1 in the middle pad MP. Bore hole B2 is aligned with the bore hole B3 (formed in rear pad RP), which in turn is always in fluid communication with tube T and bore hold B4. In the loading mode, bore hole B4 is aligned with bore hole B5 in middle pad MP and with bore hole B6 in front pad FP. An outlet port 36, connected to the aspiration pump 30, is rigidly connected with bore hole B6. Thus, through the arrangement of bore holes and grooves just described, an aspirated sample will enter port 35 through the aspiration probe attached thereto, fill the aliquoting chambers S1 and S2, and exit through the outlet port 36 and through an interconnected conduit leading to the aspiration pump.

To dispense the liquid samples in the aliquoting chambers, the middle pad MP of the shear valve assembly is rotated to the segmenting/dispensing position shown in FIGS. 3C and 3D. In this position, different groove/bore hole combinations will enable a first reagent, "Reagent 1," to chase sample aliquot S1 from bore hole B2 in the middle pad MP, and to enable a second reagent. "Reagent 2," to chase sample aliquot S2 from the external tube T and from bore holes B3 and B4. Meanwhile, and most importantly, pump 30 can continue to aspirate and dispense sample liquid from the liquid container C through the aspiration probe and through the same ports 35 and 36 through which the valve was "loaded" with liquid sample. How this is achieved is described below.

In FIGS. 3C and 3D, the liquid-sampling valve is shown in its segmenting/dispensing configuration in which the middle pad MP has rotated about 15 degrees counter-clockwise (as viewed in FIG. 3C) relative to the front and rear pads, which have remained stationary. In this mode, a liquid sample entering the entrance port 35 will again encounter groove G1, but at the opposite end of the groove from that in which the aspirated liquid encountered the groove during the loading mode. The opposite end of groove 1 is now positioned opposite bore hole B6 in the front pad. Thus, the aspirated sample entering entrance port 35 will be immediately directed through bore hole B6 which is connected to the outlet port 36. Thus, the liquid aspiration and dispense apparatus of the invention can continue to operate in the aspirating/dispense (suck and spit) mode, aspirating sample to the upstream side (i.e., the pump side) of the liquid-sampling valve, while the sampling valve has operated to position the sample aliquots S1 and S2 to be dispensed.

In rotating to its segmenting and dispensing position, the middle pad MP operates to shear aliquots S1 and S2 from the liquid path established during the loading mode, and to position such aliquots for dispensing. Dispensing of aliquot S1 is achieved by directing Reagent 1 through a first reagent entry port 40 in the front pad FP. Through a groove G3 in the front pad, the Reagent 1 path becomes aligned with bore hole B2 in the middle pad. The entering reagent chases sample aliquot S1 out of bore hole B2 through a bore hole B7 in the rear pad, and then through a first reagent exit port 42 aligned with bore hole B7. Dispensing of aliquot S2 is achieved by directing Reagent 2 through a second reagent entry port 50 extending from the rear pad RP. Port 50 is connected to a bore hole B8 in the rear pad. Upon passing through bore hold B8, Reagent 2 encounters arcuate groove G4 in the rear surface of the middle pad. Groove G4 serves to shift the fluid path of the reagent be aligned with bore hole B4 (shown in FIG. 3A). Thus, as Reagent 2 enters bore hole B4, it will expel the isolated sample aliquot S2 out through bore hole B3 formed in rear pad RP. Upon encountering a groove G5 in the rear surface of the middle pad MP, the path of the expelled sample will align with a bore hole B9 formed in the rear pad RP, and the S2 aliquot will emerge from the valve assembly through the second reagent exit port 52 which is aligned with bore hole B9. It will be noted that the liquid sampling valve is shown as comprising additional ports, grooves and bore holes, but none of the additional elements have any effect on the operation of the valve, as heretofore described.

Having described the structure and operation of a preferred liquid-sampling valve LSV comprising the liquid aspirating and dispensing apparatus 20 of FIG. 2 blood-analyzing system, the operation of the system can now be described. It is assumed that the liquid sample noted above is a whole blood sample to be analyzed in a conventional manner. Normally, before aspirating the sample, all conduits are primed with cleaning reagent or diluent. To reduce any diffusion between the aspirated sample and this cleaning reagent, a small air gap is created at the tip of the aspiration probe by momentarily activating the syringe pump 30 before the probe tip enters the sample. Thereafter, the aspirating probe is driven downward to puncture the container seal S (if the container is sealed) and to enter the whole blood sample. The syringe pump 30 is operated in a negative-pressure (sucking) mode to draw the sample through a flexible conduit 55 leading to the liquid-sample valve. As the aspiration begins, the system will begin to monitor the output of a first photoelectric blood detector BD1 which, after detecting the air gap, will monitor the integrity of the blood sample to assure the absence of any bubbles that would compromise the precision of the sample volumes to be dispensed. After the aspirated sample has advanced through the liquid-sampling valve and has exited through the outlet port 36 and into a second flexible conduit 56, a second blood detector BD2 will detect the leading air gap and signal the system's logic and control unit (LCU) that the aspirated sample has been loaded into the LSV. After confirming the detection of a blood sample by the second blood detector BD2, the LCU will energize a mechanical driver 58 adapted to cause the middle pad MP of the LSV to rotate to its sample segment/dispense position (shown in FIGS. 3C and 3D), thereby isolating sample aliquots S1 and S2 and positioning them for dispensing. A reagent pumping system (not shown) will then be activated to advance Reagents 1 and 2 into the sampling valve for the purpose of chasing the isolated sample aliquots S1 and S2 to the respective entry ports 60 of reaction chambers RC1 and RC2. Flexible conduits 61 and 62 directly connect the sample valve's outlet ports 42 and 52 to the entry ports of the reaction chambers. Meanwhile, apparatus 20 is free to operate in a suck-and-spit mode in which it is capable of dispensing virtually all of the excess sample previously aspirated to load the LSV, and of subsequently aspirating and dispensing more sample from the container or any of the reaction chambers.

As indicated above, after completing the segmentation of sample aliquots S1 and S2 by the liquid-sampling valve, the aspiration probe is ready to be moved into and out of the various reaction chambers of the system, for example, to effect movement of different liquids within the system for subsequent processing. In doing so, the syringe pump will first push the liquid sample to completely fill the aspiration probe. The syringe pump will then dispense a predetermined relatively large volume (e.g., at least 10 microliters) of liquid by controlling the movement of the syringe actuator. The sample mixing and/or delivery of additional reagent material serves to wash the sample drop from the probe tip. The reagent agitation in the reaction chamber will also assure a relatively high accuracy of the liquid dispensing, which is preferably controlled by a step motor-driven syringe pump. Before the aspiration probe moves from one reaction chamber to another, the system will wash the outside of the probe using, for example, probe washer 70 having a housing 72 in which the probe is slidably mounted. A diluent or cleansing fluid is provided under pressure to the probe-washing housing, and the resulting effluent is flushed to waste W. During the probe-washing process, the syringe pump will push out a small amount of sample to rid the probe of any contaminating reagent from the previous reaction chamber. This sample over-dispense to waste will also ensure that the liquid sample is primed to the probe tip.

In preparing some blood samples for analysis, it is common that sample preparation requires multiple steps. As indicated above, an analysis of reticulocytes often requires that these cells be selectively stained with a fluorochrome or the like. Thus, following sample segmentation in the LSV, the aspiration probe may be moved to a position in which it enters the reaction chamber RC4, which contains a fluorescent stain reagent. Upon dispensing a blood sample therein for staining, the probe may be used again, after a thorough cleaning operation, to aspirate a portion of the stained sample from reaction chamber RC4 and to transport stained sample to reaction chamber RC3 where it is precisely dispensed using, for example, a stepper motor-controlled syringe pump. Note, while a syringe pump is particularly preferred in implementing the invention, it will be apparent that any precision pumping system can be used to advance a liquid through the liquid sampling valve in opposite directions.

From the foregoing description, it may be appreciated that a highly advantageous apparatus has been devised for aspiration and dispensing liquids in an analytical instrument. The apparatus of the invention is "hybrid" in nature in that it combines both of the aforementioned BSV and suck-and-spit approaches to liquid dispensing. The apparatus of the invention has the advantageous technical effect of reducing (e.g., by as much as a factor of three) the number of liquid-sampling valves (e.g., BSV's) used in high-throughput hematology instruments since some of the liquid-sampling valves can be eliminated in favor of the far less expensive suck-and-spit approach to dispensing liquids. Further, by making use of virtually all of aspirated sample, i.e., by combining and dispensing all of the sample upstream and downstream of the LSV as one continuous sample, a given analysis may require only about one-half of the sample volume that was necessary for the same analysis using prior art apparatus for dispensing liquids in analytical instruments.

The invention has been described in detail with regard to a particularly preferred embodiment. It will be apparent, however, that many changes and variations may be made without departing from the spirit of the invention, and such changes and variations are intended to fall within the scope of the appended claims.

What is claimed is:

1. Apparatus for aspirating and dispensing a liquid sample in an automated analytical instrument, said apparatus comprising:
   (a) an aspiration probe, operably connected to a pump, and adapted to enter a sample container to aspirate a liquid sample within such container;
   (b) a transport system for selectively advancing the aspiration probe in mutually perpendicular planes so that said aspiration probe can aspirate or dispense liquid from or to different containers spaced apart; and
   (c) a liquid-sampling valve, operatively connected between said aspiration probe and pump, and comprising structure defining at least one aliquoting chamber for temporarily storing a precise volume of liquid sample to be dispensed;
   said pump being selectively operable to either (i) draw a liquid sample through said aspiration probe and through the liquid-sampling valve to fill said aliquoting chamber, or (ii) to dispense an already aspirated liquid sample through said liquid-sampling valve and through aspiration probe, said liquid-sampling valve being selectively operable in either (i) a loading configuration in which a liquid sample aspirated by the aspiration probe under the influence of the pump will pass through the liquid-sampling valve while simultaneously filling said aliquoting chamber thereof, or (ii) a segmenting/dispensing configuration in which liquid within said aliquoting chamber is positioned to be dispensed from said liquid-sampling valve by an external force, while a liquid sample can be either aspirated or dispensed through said aspiration probe and through said liquid-sampling valve by said pump.

2. Apparatus as defined by claim 1 wherein said pump is a stepper-motor controlled syringe pump.

3. Apparatus as defined by claim 1 wherein said shear valve assembly comprises a plurality of confronting and contiguous valve pads, each of said pads having structure that cooperates with structure of an adjacent pad to define different liquid flow paths within said shear valve assembly, at least one of said pads being movable with respect to the other of said pads to define either (a) a loading configuration in which a first aliquoting chamber positioned within a first flow path and becomes filled with a liquid aspirated through said aspiration probe and through said valve assembly by said pump, and (b) a segmenting/dispensing configuration in which (i) liquid within said first aliquoting chamber is positioned to be acted upon by an external force to dispense such liquid from said first aliquoting chamber along a second flow path, and (ii) liquid can be either aspirated or dispensed through said valve assembly along a third flow path by said pump.

4. The liquid-sampling valve as defined by claim 3 wherein said first aliquoting chamber is defined by a bore hole passing through one of said valve pads.

5. The liquid-sampling valve as defined by claim 4 wherein said shear valve assembly comprises three valve pads, and wherein said bore hole is formed in a middle pad of said three valve pads.

6. The liquid-sampling valve as defined by claim 3 wherein a second aliquoting chamber is positioned in said first flow path and becomes filled with liquid aspirated through said liquid-sampling valve when said liquid-aspirating valve is its loading configuration, and wherein liquid within said second aliquoting chamber is positioned to be acted upon by an external force to dispense such liquid from said second aliquoting chamber along a fourth flow path when said liquid-sampling valve is its segmenting/dispensing configuration.

* * * * *

UNITED STATES PATENT AND TRADEMARK OFFICE
CERTIFICATE OF CORRECTION

PATENT NO. : 7,661,326 B2  Page 1 of 1
APPLICATION NO. : 11/553107
DATED : February 16, 2010
INVENTOR(S) : Li et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 563 days.

Signed and Sealed this

Thirtieth Day of November, 2010

David J. Kappos
*Director of the United States Patent and Trademark Office*